United States Patent [19]

Lehmann

[11] Patent Number: 4,774,187

[45] Date of Patent: Sep. 27, 1988

[54] CELL-CULTURE APPARATUS

[75] Inventor: Jürgen Lehmann, Brunswick, Fed. Rep. of Germany

[73] Assignees: S Diessel Gmbh & Co., Hildesheim-Bavenstedt; GBF Gesellschaft fuer biotechnologische Forschung mbH, Brunswick, both of Fed. Rep. of Germany

[21] Appl. No.: 35,334

[22] Filed: Apr. 7, 1987

[30] Foreign Application Priority Data

Apr. 14, 1986 [DE] Fed. Rep. of Germany ....... 3612453

[51] Int. Cl.⁴ .......................... C12M 1/04; C12M 3/02
[52] U.S. Cl. ..................................... 435/313; 435/286; 435/287
[58] Field of Search ............... 435/313, 286, 311, 287, 435/284, 317

[56] References Cited

U.S. PATENT DOCUMENTS

| | | | |
|---|---|---|---|
| 2,970,088 | 1/1961 | Freeman | 435/311 X |
| 3,959,120 | 5/1976 | Pollock et al. | 435/313 X |
| 4,073,691 | 2/1978 | Ahnell et al. | 435/311 X |
| 4,218,538 | 8/1980 | Church | 435/313 X |
| 4,256,837 | 3/1981 | Fluri et al. | 435/287 |
| 4,476,225 | 10/1984 | Grigorian et al. | 435/287 |

Primary Examiner—Larry Jones
Attorney, Agent, or Firm—Gilbert L. Wells

[57] ABSTRACT

The invention concerns an apparatus for growing cell cultures wherein the cultures are located in at least one liquid nutrient medium and the nutrient medium or media are introduced through at least one pump-driven feed line, and where a gas (oxygen, nitrogen, air or the like) is introduced into the head room above the liquid level of the closed container, the gas pressure being kept constant in the head room, this apparatus being designed in such a manner as to prevent effectively injury to the free cells perforce ejected when evacuating the nutrient media. To that end the invention provides an overflow line communicating with the liquid in the container and terminating outside this container, its free end being located so much above the liquid level in the container that the pressure generated by the liquid column in the overflow line balances the gas pressure in the container head room.

11 Claims, 1 Drawing Sheet

CELL-CULTURE APPARATUS

BACKGROUND OF THE INVENTION

The invention concerns apparatus for growing cell cultures wherein the cultures are located within at least one liquid nutrient medium in a closed container, the nutrient medium or media being fed to the container by at least one supply line connected to a pump and a gas being supplied to the headroom above the liquid level in the closed container, such as oxygen, nitrogen, air or the like, of which the pressure is kept constant in the head room.

Nutrient media must be supplied because the nutrient medium in the container must be periodically replaced. The evacuation of the excess liquid hence must be provided for simultaneously with the supply.

In this respect it is already known to insert a pump into an evacuation line which removes as much liquid from the container as is being fed to it through the nutrient media supply line. It is further known in this regard to so control the pumps mounted in the supply and evacuation lines by a level regulating means that the evacuated amount of liquid always matches as closely as possible the one being introduced.

It is already known with respect to such level control to probe the liquid level by a sensor or else to weigh the container and to use the test values so obtained to start or shut off the pumps.

In all these known devices, the drawback is incurred that by using a pump in the evacuation line the free cells being evacuated with the nutrient liquid may be injured or destroyed by the pump, these injured cells possibly so degrading the product sought (biological molecules, proteins etc.) that either the product is not obtained at all or product manufacture becomes uneconomical.

SUMMARY OF THE INVENTION

Accordingly it is the object of the invention to so design an apparatus of the initially cited kind that the drawbacks of the known designs are avoided and in particular that injury to the free cells undesired per se and forced to be evacuated shall be effectively prevented.

This problem is solved by the invention by providing an overflow line communicating with the liquid in the container and terminating outside this container, the free end of this overflow line being so much above the liquid level in the container that the pressure generated by the liquid column in the overflow line balances the gas pressure in the container head room.

Such a design achieves the elimination of pumps and other mechanical parts otherwise required for evacuation, because the pressure-fed nutrient media increase the gas pressure in the container head room, whereby the amount fed is automatically again evacuated through the overflow line. As a result injury to the evacuated free cells which now merely need slide along the line inner walls, will be practically excluded.

It is especially appropriate that the free end of the overflow line issue into an open overflow vessel comprising in turn a discharge stub communicating by a discharge line with a collecting vessel receiving the product.

The overflow vessel must be open to prevent pressure from building up in the discharge line that would then interfere with the discharge. Appropriately the aperture of the overflow vessel communicates with a branch line enclosing a sterilization filter, the branch line being open beyond this sterilization filter.

Advantageously furthermore both the overflow line and the discharge line to the collecting vessel will be at least flexible in part so that it shall be possible when manually compressing the lines to eliminate any clogging or the like without thereby injuring the free cells.

The free end of the overflow line may be height-adjustable whereby it will be possible to change the pressure level and hence the amount of supplied medium. This represents the substantial advantage that the pressure in the head room is arbitrarily selectable by displacing the free end of the overflow line. This assumes special significance when using membranes to gas the liquid in the container, formation of gas bubbles in the membrane pores depending on the pressure outside the membrane.

The end of the overflow line on the side of the container may dip directly into the liquid in the container beyond the liquid level; however a branch line connected to the lower area of the container may also be used, ending below the liquid level, the overflow line end on the side of the container being connected to this branch line. The difference in levels betwen the liquid and the free end of the overflow line remains unaffected thereby.

The gas pressure in the head room is appropriately kept constant by a pressure-regulating valve mounted in the discharge line.

BRIEF DESCRIPTION OF THE DRAWINGS

The invention is elucidated further below in relation to illustrative embodiments shown in the drawing.

DESCRIPTION OF ITS PREFERRED EMBODIMENT

Figure 1:
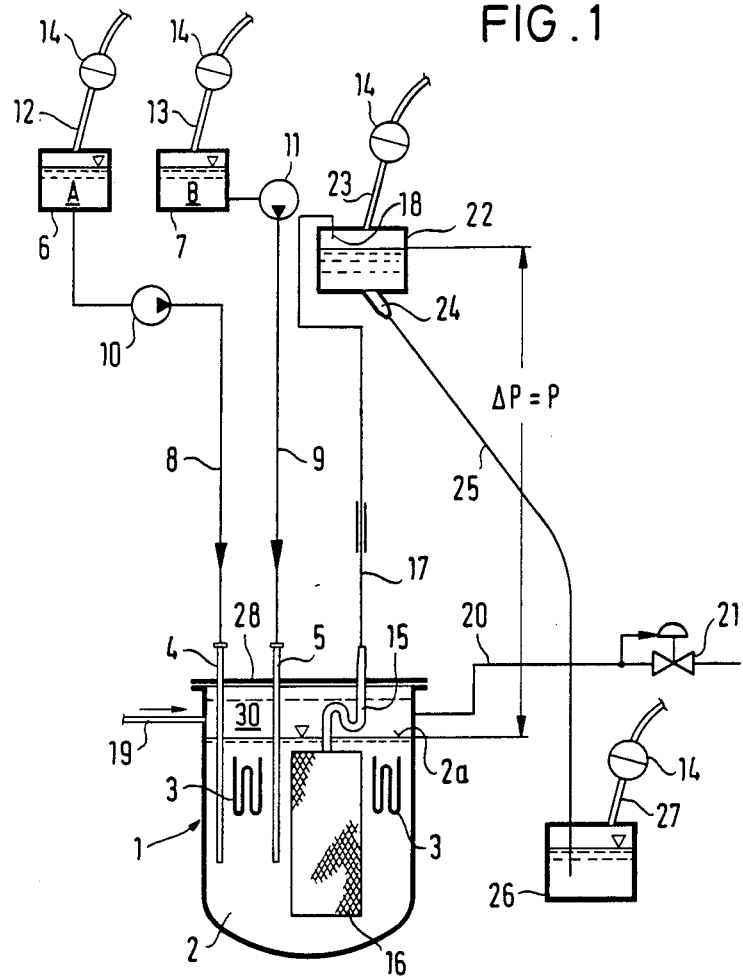
FIG. 1 is a schematic view of an illustrative embodiment of the apparatus of the invention and, FIG. 2 shows the container of FIG. 1 for a variation of the embodiment.

As shown in FIG. 1, a container 1 is provided which holds cell cultures to be grown in a nutrient liquid 2. Illustratively the liquid 2 may be gassed using membrane hoses 3.

Because the nutrient liquid 2 in the container 1 must be periodically replaced, tubes 4 and 5 are provided which dip into the liquid and through which nutrients A and B held in open reservoirs 6 and 7 may be fed to the liquid 2 in container 1. This supply is carried out using pressure applied through peristaltic pumps 10 and 11 mounted in the feed lines 8 and 9.

The reservoirs 6 and 7 communicate through branch lines 12 and 13 with the atmosphere, sterilizing filters 14 being inserted in the branch lines.

A gooseneck hose piece 15 is provided for the liquid discharge, also dipping by its lower end in the liquid 2, a screen 16 being mounted between the dipping end of the hose piece 15 and the liquid 2 within this liquid. Lastly an overflow line 17 connects to the hose piece 15 and has a free end 18 so much above the liquid level 2a in the container 1 that the pressure generated by the liquid column in the overflow line 17 balances the pressure in the head room 30 of the container 1.

The pressure in the head room 30 of container 1 is generated by the introduction of a gas (oxygen, nitrogen, air or the like), this introduction being indicated in FIG. 1 by the line 19. The pressure so generated in the head room 30 is kept constant by a pressure regulating valve 21 in the discharge line 20.

The free end 18 of the overflow line 17 issues in the manner shown into an open overflow vessel 22 of which the opening in the illustrative embodiment communicates with a branch line 23 into which again a sterilizing filter 14 is inserted.

The overflow vessel 22 comprises a discharge stub 24 connected through a discharge line 25 with a collecting vessel 26 receiving the product. This vessel 26 also is open by means of a branch line 27 with inserted sterilizing filter 14.

The free end 18 of the overflow line advantageously can be height-adjusted either within this overflow vessel 22 or together with it. In this manner the pressure in the head room 30 of container 1 is adjustable and selectable.

The described apparatus operates as follows:

On account of the gas supply into the head room 30 of the container 1 closed by the cover 28, a gas-formed pressure cushion is formed in the head room 30 and kept constant by the pressure regulating valve 21. If now nutrient medium is fed from the reservoirs 6 and/or 7 by means of the pumps 10 and/or 11 through the lines 8 and 9 against the pressure prevailing in the head room 30, then a rise in pressure will take place in the head room 30 whereby the liquid column in the overflow line 17 is displaced upward so that the amount of liquid fed through the lines 8 and/or 9 discharges at the free end 18 of the overflow line 17 into the overflow vessel 22 and from there passes into the collecting vessel 26. Accordingly the liquid discharge takes place in the absence of any moving parts and the discharged cells cannot be injured.

Figure 2:
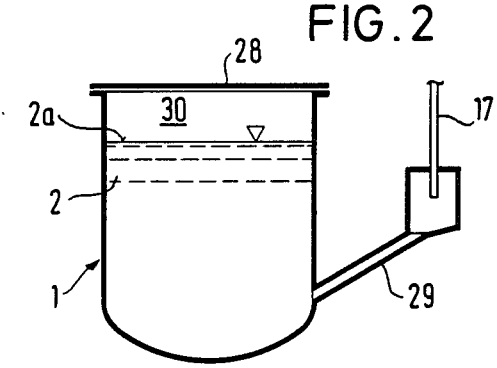

FIG. 2 shows a somewhat altered embodiment mode wherein a branch line 29 is connected below the liquid level 2a to the container 1, the container-side end of the overflow line 17 communicating with this branch line. Again the difference in levels between the liquid level 2a and the free end 18 of the overflow line 17 is determinant for the particular amount of liquid to be discharged.

I claim:

1. An apparatus for growing cell-cultures comprising:
   (a) a closed container containing said cell-cultures present within at least one liquid nutrient medium at a given level in said closed container;
   (b) pump driven supply means for feeding said nutrient medium into said closed container;
   (c) means for introducing a gas into said closed container into a head room above said given level;
   (d) means for maintaining constant gas pressure in said head room;
   (e) a second container open to atmospheric pressure positioned above said closed container;
   (f) an overflow line having a first end below said given level in said closed container and a second end in said second container; and
   (g) said second end positioned a given vertical distance above said given level generating a liquid column pressure in said overflow line balancing said constant gas pressure in said head room of said closed container.

2. The apparatus of claim 1, wherein said second end is a free end (18) of said overflow line (17) issuing into said second container comprising an open overflow vessel (22) which in turn comprises a discharge stub (24) communicating through a discharge line (25) with a collecting vessel (26) receiving a product.

3. The apparatus of claim 2, wherein a first branch line (23) with an inserted sterile filter (14) and open beyond this sterile filter (14) is connected to an opening of said overflow vessel (22).

4. The apparatus of claim 3, wherein both said overflow line (17) and said discharge line (25) to said collecting vessel (26) are flexible at least in part.

5. The apparatus of claim 4, wherein said free end (18) of said discharge line (17) has means for adjusting the height.

6. The apparatus of claim 5, wherein said free end (18) of said discharge line (17) has means for height-adjustment within said overflow vessel (22).

7. The apparatus of claim 6, wherein said first end of said overflow line (17) dips directly into liquid (2) contained in said closed container (1) below said given level.

8. The apparatus of claim 5, wherein said free end (18) has means for height-adjustment jointly with said overflow vessel (22).

9. The apparatus of claim 7, wherein said first end of said overflow line (17) dips directly into liquid (2) in said closed container (1) below said given level (2a).

10. The apparatus of claim 7, wherein a second branch line (29) is connected to a lower area of said closed container (1) and terminates below said given level, said first end of said overflow line (17) being connected to said second branch line (29).

11. The apparatus of claim 10, wherein said means for maintaining gas pressure in said head room (30) comprises a pressure regulating valve (21) in a discharge line (20) connected to said closed container.

* * * * *